(12) United States Patent
Dedo

(10) Patent No.: US 6,537,298 B2
(45) Date of Patent: Mar. 25, 2003

(54) TOURNIQUET PADDING (76) Inventor: Richard G. Dedo, 175 Denise Dr., Hillsborough, CA (US) 94010

(*) Notice: Subject to any disclaimer, the term of this patent is extended or adjusted under 35 U.S.C. 154(b) by 80 days.

(21) Appl. No.: 09/795,606

(22) Filed: Feb. 28, 2001

(65) Prior Publication Data

US 2002/0120288 A1 Aug. 29, 2002

(51) Int. Cl.[7] .............................................. A61B 17/135
(52) U.S. Cl. ...................................................... 606/203
(58) Field of Search ............................. 128/132 R, 327; 604/290, 202, 203

(56) References Cited

U.S. PATENT DOCUMENTS

| 4,302,495 A | 11/1981 | Marra | 428/110 |
|---|---|---|---|
| 4,348,444 A | 9/1982 | Craig | 428/137 |
| 4,406,281 A | 9/1983 | Hubbard et al. | 128/132 |
| 4,422,837 A | 12/1983 | Rasmussen | 425/289 |
| 4,762,123 A | 8/1988 | Dedo | 128/153 |
| 4,820,279 A | 4/1989 | Dedo | 604/290 |
| 5,180,359 A | 1/1993 | Dedo | 602/6 |
| 5,411,518 A | 5/1995 | Goldstein et al. | 606/202 |
| 5,413,582 A | 5/1995 | Eaton | 606/202 |
| 5,690,672 A | * 11/1997 | Cohen | 606/203 |
| 5,733,304 A | * 3/1998 | Spence | 606/203 |
| 5,823,012 A | * 10/1998 | Hacskaylo | 2/170 |
| 5,968,072 A | * 10/1999 | Hite et al. | 606/202 |
| 6,027,465 A | 2/2000 | Scholz et al. | 602/6 |
| 6,100,206 A | 8/2000 | Scholz et al. | 442/42 |
| 6,132,835 A | 10/2000 | Scholz et al. | 428/68 |
| 6,361,548 B1 | * 3/2002 | McEwen | 606/201 |

* cited by examiner

Primary Examiner—Ismael Izaguirre
(74) Attorney, Agent, or Firm—Whyte Hirschboeck Dudek SC (57) ABSTRACT Tourniquet padding and methods of its use with a tourniquet are provided. The tourniquet padding comprises a soft, compressible material with an interrupted adhesive areas that are applied against the skin. The tourniquet can be made with and without an internally positioned padding material. The tourniquet padding has a width wider than the tourniquet to provide an extension of material along the distal edge with adhesive that is applied to the skin, and an overlying layer that is turned onto and adhered to the tourniquet to provide a protective surface and keep the tourniquet from slipping distally down the limb during use. The overlying layer can include perforations to divide it into sections. As the tourniquet inflates and deflates, the overlying layer flexes to accommodate the change in thickness. The tourniquet padding can also be crimped or pleated along a proximal edge to accommodate a range of circumferences of extremities. The device can also include a layer of plastic or other liquid-repellent material over the leading or distal edge to protect it from becoming wet during a medical procedure, or affixed to the overlying layer to protect the tourniquet from becoming wet or soiled.

36 Claims, 10 Drawing Sheets

TOURNIQUET PADDING

FIELD OF THE INVENTION

The present invention relates to disposable padding for use in the medical field, and more particularly to padding used in connection with blood pressure cuffs and other tourniquets.

BACKGROUND OF THE INVENTION

Tourniquets are used by orthopedists, anesthesiologists and other medical practitioners to stop the flow of blood through an artery by compression, and are typically placed proximally on an upper or lower extremity such as the upper arm or thigh, and occasionally in a more distal position such as on the calf. Inflatable tourniquet cuffs are commonly used in the medical field, and include bladders that are inflated by compressed air, producing enough compression to occlude the arterial flow. For an orthopedist or other surgeon who does extremity surgery, this achieves an avascular, or "non-bleeding," dry surgical field. By stopping the flow of blood into the extremity, surgery can be performed in that extremity distal to the tourniquet without bleeding. With the artery occluded, no blood flows into the surgical field and the surgeon can perform surgery in what is temporarily an avascular area.

To completely stop the flow of blood, a tourniquet should be applied as high as possible into the axilla or "armpit" in an upper extremity, or into the groin adjacent to the inguinal ligament located at the crease between the lower abdomen and the anterior, or front part of the top of the thigh. Such placement occludes the artery before it begins to divide into its branches, and provides a surgeon with a large operative field for elbow and knee surgery. A large area is needed in order to prep the skin adequately and to drape the area properly so that during surgery, if an incision needs to be extended, the surgeon does not need to cut through drapes to do so.

Tourniquets in the form of blood pressure cuffs, are also used by anesthesiologists to monitor blood pressure during surgical procedures, by nurses in intensive care units, by medical personnel in transitional care units, among others. A blood pressure cuff is often applied and left on for an extended time period, i.e., several days. The cuff is applied as high as possible on the upper extremity in order to more effectively occlude the artery before it branches and obtain a more accurate blood pressure measurement.

In use during a surgical procedure, a tourniquet is applied with continuous pressure for an extended period of time. In the use of a blood pressure cuff during a surgical procedure or in an intensive care or cardiac care unit, the cuff is automatically and repeatedly inflated and deflated at about one to two minute intervals to monitor blood pressure, and can be left on for several days. This adds up to numerous compressions of the skin during a procedure or treatment period.

Tourniquets are commercially available and typically 2 to 6 inches wide for single bladder tourniquets and about 8 to 9 inches wide for double bladder tourniquets ("Bier blocks"). A blood pressure cuff about 4 inches wide is used most frequently by anesthesiologists. For an average size patient, a 4-inch wide tourniquet is used for upper extremity surgery, while a 4- to 6-inch wide tourniquet is typically applied to the thigh for surgeries on the lower extremities.

Tourniquets are generally supplied without padding, and some surgeons and anesthesiologists use a tourniquet without padding underneath. However, this can result in injury to the skin caused by prolonged or intermittent pinching while the surgery is performed or when the blood pressure tourniquet is inflated/deflated to monitor blood pressure.

To avoid skin irritation and damage to the outer layers of the skin by the repeated compression, a soft padding material is typically wrapped around the extremity and the tourniquet is applied over the wrapped material. Typically, 3 to 4 layers of sheet wadding or cast padding such as WEBRIL™ cotton padding (Kendall Company) is used under the tourniquet.

Although desirable, the use of padding under a tourniquet is problematic. The diameter or circumference of the upper arm and thigh decreases from the proximal end (i.e., shoulder, hip) to the distal end (i.e., elbow, knee). In most people, the upper arm and thigh are conically shaped like an ice cream cone, being wider at the top and narrowing toward the elbow or knee. This presents problems in maintaining a tourniquet in a stationary position on the upper part of the arm or the upper part of the thigh. Although the cushioning effect of the padding is a plus, the padding tends to slip distally down the extremity during a procedure. This situation becomes more problematic as the weight of the person increases and the distal part of the extremity is proportionately smaller than the proximal part. In addition, a heavier patient tends to have looser skin and subcutaneous tissues, requiring a higher amount of compression to occlude the artery for surgery or to obtain blood pressure.

Slippage of a blood pressure cuff along a limb causes particular problems for anesthesiologists and surgeons. For surgical procedures, the tourniquet cuff is applied to the upper arm and inflated, blood pressure is recorded, and the cuff is then deflated. As this is repeated over an extended time during the procedure, the cuff slips distally and a different part of the extremity becomes compressed. This change in the location where the blood pressure measurements are taken can result in inaccurate readings.

There have also been numerous complaints about tourniquet slippage down the arm or thigh and causing problems with proper occlusion of the artery during surgical procedures. For a surgical operation performed on an elbow, knee, forearm, hand, calf or foot, as the tourniquet slips distally, compression decreases and compromises the surgical field with bleeding. In addition, the distal edge of the tourniquet is not sterile, and as the edge enters the surgical field, the potential for post-operative infection increases. There have also been problems with the tourniquet or cuff slipping off the underlying padding material onto the skin, resulting in blisters where the skin had been pinched.

Another problem arises when the tourniquet is applied over several layers of cast padding, and the limb is prepped with a wet surgical scrub. An extremity is typically elevated while it is being prepped by a scrub nurse, and fluid that runs up the arm or leg wets the tourniquet and/or tourniquet padding. Most surgical preps include skin irritants and are applied and then wiped or rinsed off the skin. Consequently, compression by a wet padding and prolonged contact with a pre-operative skin prep can result in serious damage to the outer layers of the skin.

In addition, tourniquets that become soiled with blood or other fluids are difficult to clean thoroughly and, in cases of AIDS and other infectious diseases, the contaminated tourniquet is usually discarded. With the cost of tourniquets at about $200 and higher, this can significantly increase the cost of a surgery or other medical procedure.

Therefore, it would be desirable to provide a padding that can be used in connection with a blood pressure cuff and other tourniquets that overcome the foregoing problems.

SUMMARY OF THE INVENTION

The present invention provides a tourniquet padding designed to deal with the foregoing problems of anesthesiologists and surgeons who use tourniquets.

In one aspect, the invention provides a tourniquet padding for use with a tourniquet. The padding comprises a soft, compressible material with an interrupted adhesive surface to be applied against the skin. The tourniquet padding has a length sufficient to be wrapped around a limb of a person, and a width wider than the tourniquet. An extension of material on the lower or distal edge of the tourniquet padding with an adhesive surface is applied to the skin, and a second outer layer is turned proximally over the lower edge of the tourniquet to protect the tourniquet, and to keep it from slipping distally. The present tourniquet padding advantageously holds a blood pressure cuff or other tourniquet in place on a limb and prevents it from slipping down the limb during use.

The portion of the tourniquet padding to be turned proximally onto the tourniquet preferably includes perforations or slits provided at suitable intervals that allow it to be divided or split to accommodate a range of sizes of tourniquets, and/or the inflation/deflation of the tourniquet during use. In another embodiment, the tourniquet padding may be crimped or pleated along a proximal edge to make it slightly elastic, in order to accommodate extremities (arm/leg) of varying circumferences.

In a preferred embodiment, the tourniquet padding also includes a layer of plastic or other liquid-repellent material to cover the distal edge and at least a portion of the outer surface of the cover sheet that is placed against the skin. This protects the padding from becoming soaked by prep solutions and other liquids that are applied to the limb.

In another aspect, the invention provides methods for using the tourniquet padding with a blood pressure cuff or other tourniquet. The tourniquet padding is wrapped around a limb of a person and the adhesive areas are applied to the skin. A tourniquet is then positioned over the tourniquet padding and wrapped around the limb such that the distal edge of the tourniquet padding extends beyond the distal edge of the tourniquet. The inner layer of the extension of the tourniquet padding is adhered to the skin, and the outer layer of the extension is folded onto and adhered to the tourniquet to secure the tourniquet in place on the padding. Desirably, the outer layer of the extension includes perforations or slits to separate the extension into sections that are folded onto the tourniquet. The tourniquet can then be inflated and deflated as required by the medical procedure.

In yet another aspect, the invention provides a cover sheet useful in making a tourniquet padding as provided according to the invention. The sheet is preferably made of conformable material having adhesive on an outer surface along a distal edge, and perforations to separate the distal edge into sections or flaps. The width of the sheet is desirably wider than a tourniquet such that a portion of the sheet along the distal edge may be folded onto and adhered to the tourniquet when positioned on the sheet, and the proximal edge of the sheet will extend beyond the proximal edge of the tourniquet. Preferably, the cover sheet comprises a scrim reinforced material having fibers or filaments that are preferably at least partially embedded in the material and interwoven in a grid pattern in an open mesh web. Optionally, the sheet can be gathered along the proximal edge.

In another embodiment of a cover sheet, the sheet can comprise an elongate sheet of conformable material, preferably a scrim reinforced material, that is folded into at least three layers, including two cover sheets and one or more inner layers. Each of the cover sheets has adhesive on the outer surface along a distal edge. One cover sheet includes one or more adhesive areas on the proximal outer surface. The other cover sheet has perforations to separate the distal edge into sections.

BRIEF DESCRIPTION OF THE DRAWINGS

Preferred embodiments of the invention are described below with reference to the following accompanying drawings, which are for illustrative purposes only. Throughout the following views, the reference numerals will be used in the drawings, and the same reference numerals will be used throughout the several views and in the description to indicate the same or like parts.

DETAILED DESCRIPTION OF THE PREFERRED EMBODIMENTS

The present invention encompasses a tourniquet padding for use with a tourniquet, and methods for making and using the tourniquet padding.

As used herein, the term "upper extremity" refers to the "arm" of a person including the shoulder, arm, elbow, forearm, wrist and hand. The term "lower extremity" refers to the "leg" of the person including the hip, thigh, knee, calf, ankle and foot.

A first embodiment of a tourniquet padding 10 of the present invention is described with reference to FIGS. 1–5. As shown, the tourniquet padding 10 comprises a padding material 12 disposed between a first (outer) cover sheet 14 and a second (inner) cover sheet 16. As depicted, the cover sheets 14, 16 are formed from a unitary sheet that is folded into at least three overlying layers to form the two cover sheets and one or more inner sheets 17. The padding layer 12 is positioned between the second cover sheet 16 and the inner sheet and provides a cushioning effect. In any of the embodiments described herein, the cover sheets and inner sheets can also comprise separate, individual sheets (not shown) placed on opposite sides of the pad. In addition, the padding layer 12 can be omitted, and the tourniquet padding can be used as an underlayer beneath a tourniquet to maintain the tourniquet in place and prevent it from slipping down the extremity, and/or as a covering to keep the tourniquet clean.

Each of the cover sheets 14, 16, has an inner surface 18, 20, an outer surface 22, 24, a length 26, 28, a width 30, 32, a first side edge 34, 36, a second side edge 38, 40, a distal edge 42, 44, and a proximal edge 46, 48. In use, as further discussed below, the tourniquet padding 10 is typically wrapped around a limb such that the second (inner) cover sheet 16 is applied against the skin 49 (FIGS. 5A–5B), and the distal edge 54 of the padding is oriented in the direction of the distal portion of the limb, i.e., the hand or foot. The proximal edge 56 of the tourniquet padding 10 is then oriented toward the proximal end of the limb, i.e., the shoulder or groin.

Figure 1:
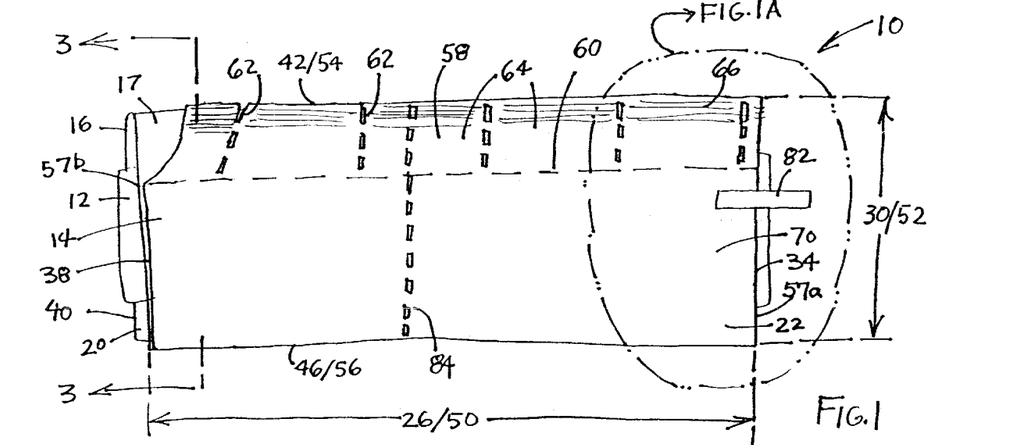
FIG. 1 is a front perspective view of an embodiment of a tourniquet padding of the invention.

Referring to FIG. 1, the distal portion 58 of the first (outer) cover sheet 14 is foldable along a fold line 60 at its distal edge 42. The first cover sheet 14 can include scoring or indicia such as lining or arrows running longitudinally to indicate the fold line 60 (and where the inferior or distal edge of the tourniquet would be placed).

Figure 1A:
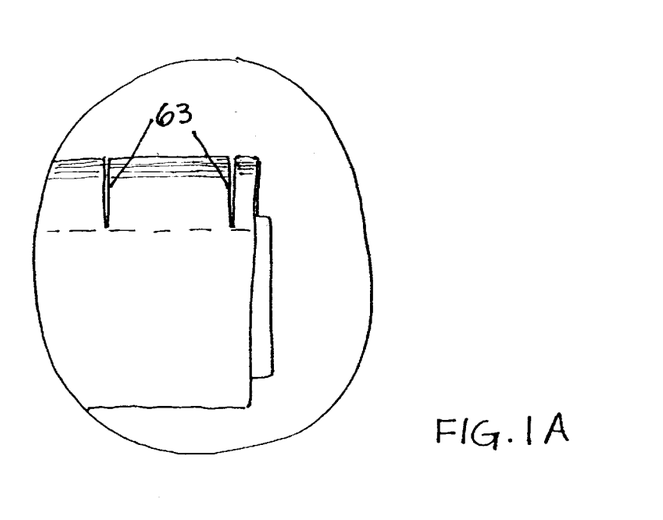
FIG. 1A is a fragmentary view of the tourniquet padding of FIG. 1 showing the incorporation of slits in the cover sheet.
Figure 4:
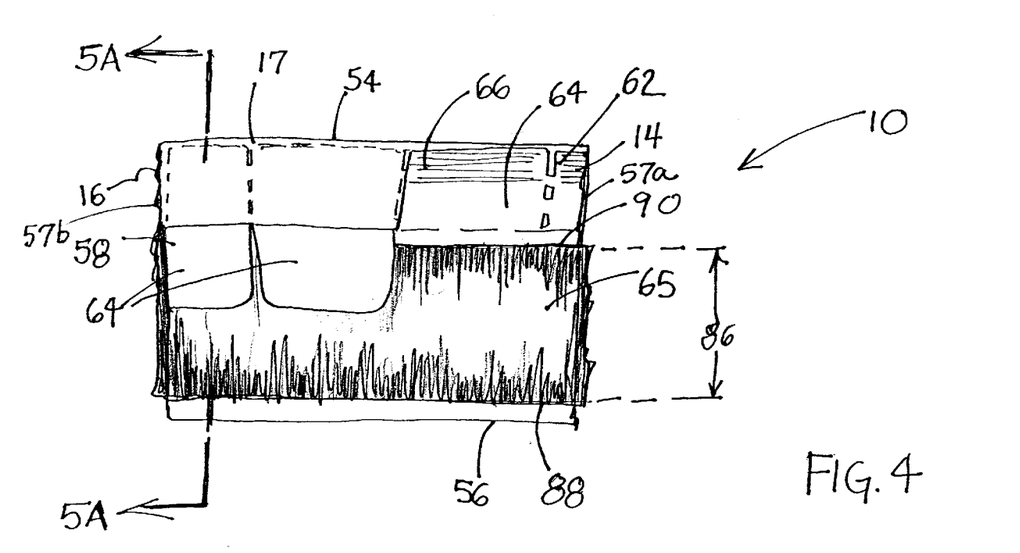
FIG. 4 is a front perspective view of the tourniquet padding of FIG. 1 with a tourniquet positioned thereon.
Figure 5A:
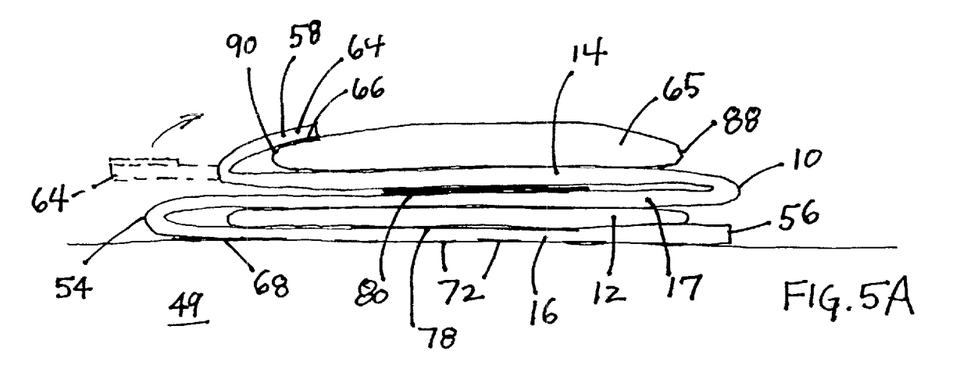
FIG. 5A is a side view of the tourniquet padding and tourniquet of FIG. 4, taken along lines 5A—5A showing placement of a portion of the tourniquet padding onto the tourniquet.
Figure 5B:
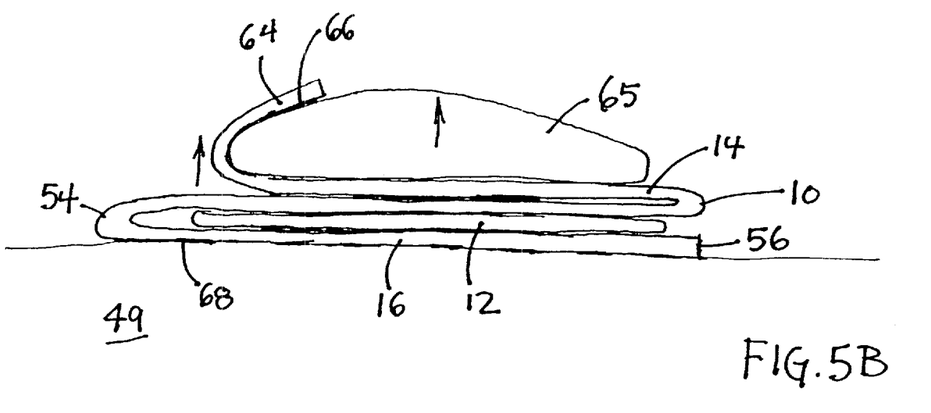
FIG. 5B is a side view of the tourniquet padding and tourniquet of FIG. 5A, showing the tourniquet inflated during use.

It is also desirable that the first cover sheet 14 includes perforations 62, or slits 63 as shown in FIG. 1A, that are spaced apart at regular intervals along the length 26 of the distal edge 42, for separating the distal edge into sections or flaps 64. In use, as shown in FIG. 4, the distal portion 58 of the cover sheet 14 is turned proximally over a tourniquet 65 positioned on the cover sheet 14 near the fold line 60. The perforations 62 or slits 63 allow the cover sheet 14 to separate and accommodate the changing size (i.e., thickness) of the tourniquet 65 as it inflates and deflates. As depicted in FIGS. 5A–5B, the distal portion 58 of the first (outer) cover sheet 14 lifts upward as the tourniquet inflates while the second (inner) cover sheet 16 remains secure to the skin 49. This arrangement advantageously avoids pulling on the second cover sheet 16 and the underlying skin 49 so that there is little or no blistering of the skin as the tourniquet is inflated and deflated.

Figure 2:
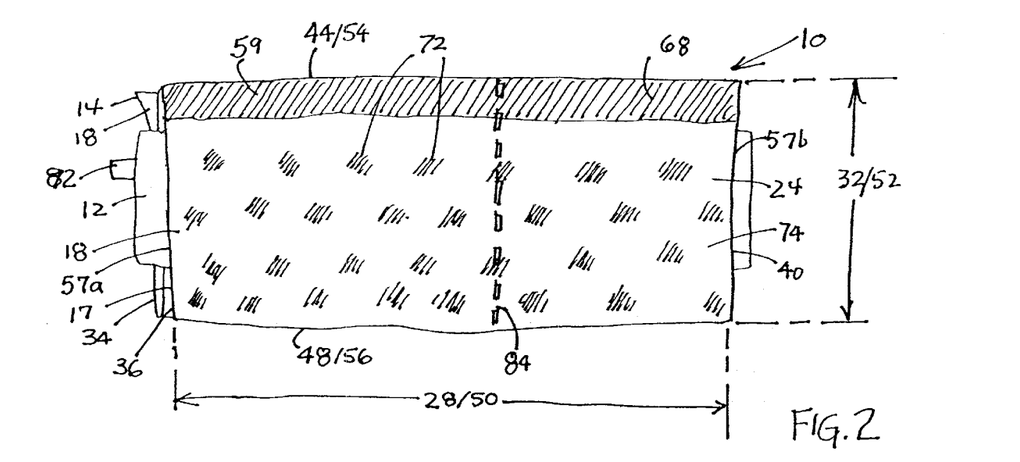
FIG. 2 is a rear perspective view of the tourniquet padding of FIG. 1.
Figure 3:
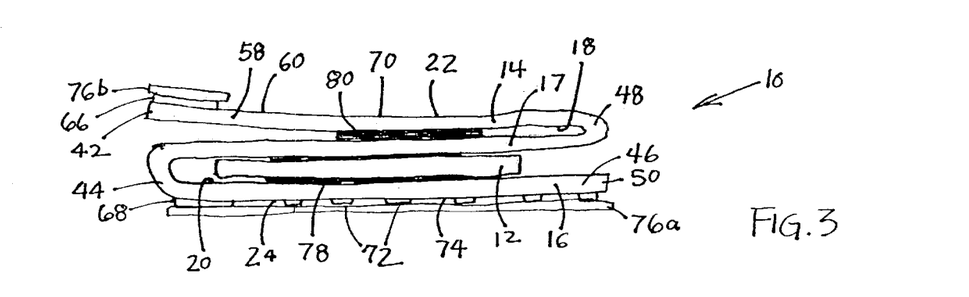
FIG. 3 is a side view of the tourniquet padding of FIG. 1, taken along lines 3—3.

Referring to FIGS. 1–3, adhesive material is applied along the distal edges 42, 44 of the outer surfaces 22, 24 of the cover sheets 14, 16. The adhesive is applied as a strip or band 66, 68, along the length 26, 28 of the cover sheets, and can be in the form of a solid band, intermittent lines, dots or other discrete or disconnected segments, and the like. The strip of adhesive 66 along the edge 42 of the first cover sheet 14 is typically about 0.5 to about 1 inch wide, and sufficient to securely adhere the distal portion 58 of the first cover sheet 14 on the surface of a tourniquet 65 and maintain the tourniquet in position on the padding 10 during use. Although not shown, the proximal surface area 70 of the first (outer) cover sheet 14 can further comprise a solid layer or lines or other discrete areas of adhesive to hold the tourniquet in place on the cover sheet 14 during use.

As depicted in FIG. 2, the second (inner) cover sheet 16 includes a strip of adhesive 68 along the distal edge 44, and one or more discrete areas 72 of adhesive such as oblique/vertical strips and/or spots or spaced apart areas arranged over its proximal surface area 74. The strip of adhesive strip 68 and the adhesive areas 72 are sufficient to adhere the tourniquet padding 10 to the skin 49, and inhibit the padding and tourniquet from slipping along a limb during use. The strip of adhesive 68 is typically about 0.5 to about 1 inch wide. It is preferred that adhesive is not applied as a solid layer over the proximal surface area 72 of the second cover sheet 16 because, as the tourniquet is inflated, it would pinch the skin as the circumference of the extremity is decreased in size by compression of the tourniquet. The strip of adhesive 68 along the distal edge 44 of the cover sheet can comprise a solid band of adhesive because that section of the tourniquet padding is not compressed during inflation of the tourniquet.

The adhesive material that is used in conjunction with the tourniquet padding, particularly on the second (inner) cover sheet 14 that is placed against the skin, is preferably a biocompatible and hypoallergenic adhesive material that is adherable to skin but will release from the skin with minimal trauma. Such adhesives are well known in the art and commercially available. Useful adhesives include, for example, acrylic adhesives that are used in surgical applications where reduced skin trauma is required. Preferably, the adhesive is a pressure-sensitive adhesive substance.

As shown in FIG. 3, it is also desirable that the adhesive surfaces are protected by a suitable removable covering or releasably attached release sheet 76a–b. For example, a release sheet 76a can be applied as a cover over the entire surface of the cover sheet, as a longitudinal strip 76b over the adhesive band 66 along the edge 42 of the cover sheet 14, or a panel section (not shown) over the proximal surface areas 70, 74 of the cover sheets, and combinations thereof. The release sheets 76a, 76b can then be peeled off just prior to applying the tourniquet padding to the limb. In an embodiment in which the first cover sheet 14 includes slits 63, as depicted in FIG. 1A, an overlying peel-off layer 76b placed over the adhesive 66 can serve to maintain the sections 64 in place before being applied to the tourniquet.

The cover sheets 14, 16 provide a flexible yet strong covering over the inner padding 12, and can be manufactured from any suitably compliant, natural or synthetic (man-made) material including but not limited to, paper, a reinforced scrim material, cloth, terry cloth, cheesecloth, and the like, and combinations thereof. Preferably, the cover sheets are composed of a material that is porous to pass moisture, vapor and air.

A preferred material comprises a lightweight conformable scrim reinforced material that allows the tourniquet padding to readily flex and bend about the extremity. Scrim reinforced materials are well known and widely used, and comprise threads or filaments. Preferably, the scrim fibers or strands are embedded or partially embedded in the material, and are preferably interwoven at about right angles in an open mesh web or grid. Suitable scrims can be made from paper, knits, wovens, non-wovens and extruded porous sheets such as materials available from Conweb, Minneapolis, Minn. Examples of suitable scrim filaments include fiberglass and ceramic fibers, and fibers made of polyester, polyethylene and other polyolefins, polyacrylate, rayon, cotton, hemp, jute, natural rubber, polyurethane, and blends thereof. Scrim materials are also described, for example, in U.S. Pat. Nos. 6,027,465, 6,100,206, and 6,132,835 (Scholz et al., 3-M Company), the disclosures of which are herein incorporated by reference.

The padding layer 12 provides a cushioning sufficient to prevent the skin of a person from being pinched by a tourniquet 65 mounted on the tourniquet padding 10 and wrapped around a limb of the person. Typically, as shown, no padding is provided in the distal portions 58, 59 of the cover sheets 14, 16. The padding 12 can comprise a porous or non-porous material, or a natural or synthetic fiber material. A desirable padding material is cast padding, which can be made from cotton, nylon, rayon, acrylic, polyester, and other like materials and blends. Other suitable materials include a paper material, a scrim reinforced material, a foamed material such as a polyurethane foam, or other material having memory that will return to its pre-compressed shape after being compressed, and combinations thereof.

Preferably, the materials used in making the tourniquet padding are sterilizable. As such, the tourniquet padding can be sterilized and packaged to provide a clean surface along the edge of a surgical field adjacent the tourniquet.

In assembling the cover sheets 14, 16 and the padding layer 12, it is desirable to bond the padding layer to at least the second cover sheet 16, as depicted by the adhesive area 78 in FIG. 3. The padding can be attached to the cover sheet(s), for example, with an adhesive, by stitching and/or by thermal bonding. Optionally, but preferably, at least a portion of the inner surface of the first (upper) cover sheet (proximal to the fold line) is bonded to the inner layer, for example by adhesive areas 80, as shown in FIG. 3. Adhesive is then applied onto the outer surfaces of each cover sheet along the distal edge and onto one or more areas of on the outer surface of the second cover sheet, and a cover sheet is applied over the adhesive areas.

The tourniquet padding 10 can optionally include a member 82 such as an adhesive tab attached at either or both of the side edges 14, 16 for securing the end of the tourniquet padding 10 together around the limb.

The length 50 of the tourniquet padding 10 is sufficient to allow the padding to be wrapped around the limb, with the side edges 34/36, 38/40 of the cover sheets 14, 16 meeting up or overlapping. Since the length 50 that is needed will vary according to the application, it is desirable to provide the tourniquet padding in rolls. Typically, for an adult, the tourniquet padding 10 ranges between approximately 8 inches to approximately 26 inches in length. The padding 10 can be cut from the roll to a desired length, or can include perforations 84 at intermittent locations along the length, as shown in FIGS. 1–2, which extend through the cover sheets 14, 16 and padding 12 to allow the tourniquet padding 10 to be separated into sections.

Tourniquets vary in width and are generally available in widths of 2, 4 or 6 inches. Dual bladder ("Bier blocks") and other specialized tourniquets can be, for example, 8 to 9 inches in width. In the use of a Bier block tourniquet, the proximal bladder is inflated, a local anesthetic is injected into a vein, and the arm is elevated to cause the anesthetic to migrate proximally to the edge of the proximal tourniquet, which produces numbness in the extremity. The second tourniquet is inflated over an anesthetic area of the arm, and the proximal tourniquet is deflated. This arrangement substantially eliminates tourniquet pain.

The width 52 of the tourniquet padding 10 can be varied to accommodate the width 86 of the tourniquet 65. In general, the width 52 of the tourniquet padding is sufficient to receive a tourniquet thereon such that there is no or a minimal amount of contact of the tourniquet with the skin in order to minimize pinching of the skin during the inflation/deflation of the tourniquet, and/or trauma to the skin from contact of the proximal edge of the tourniquet.

Referring to FIGS. 4 and 5A–5B, in use, a tourniquet 65 is positioned on the tourniquet padding 10 such that the distal portion 58 of the first (outer) cover sheet 14 may be folded over at least a portion of the tourniquet. Preferably, the tourniquet padding 10 is wider than the tourniquet such that when the first cover sheet 14 is folded onto the tourniquet, the proximal edge 56 of the tourniquet padding extends beyond the proximal edge 88 of the tourniquet. For example, in the use of a tourniquet 65 that is about 4 inches wide, the tourniquet padding is preferably at least about 5½ inches wide so that, in positioning the tourniquet on the padding, at least about ½-inch of the tourniquet padding extends beyond the proximal edge 88 of the tourniquet, and at least about 1-inch of the tourniquet padding extends beyond the distal edge 90 of the tourniquet. In addition, either cover sheet can be as wide or wider than the other cover sheet.

Figure 6:
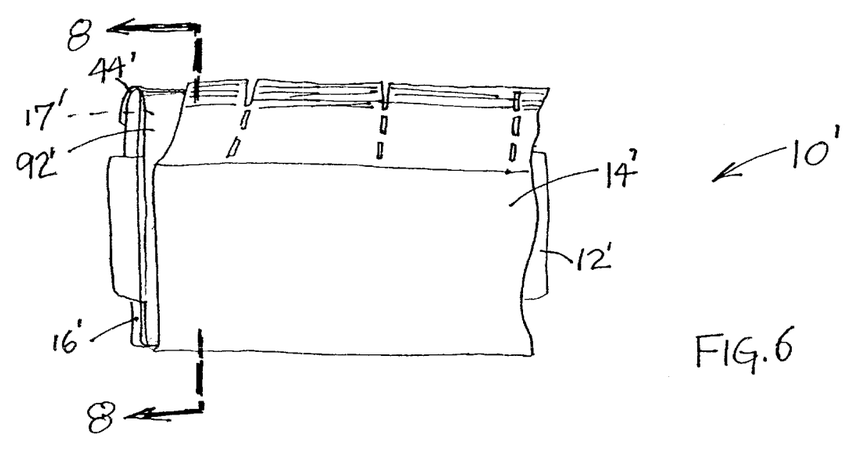
FIG. 6 is a front perspective view of another embodiment of a tourniquet padding of the invention that includes a liquid-impermeable layer.
Figure 7:
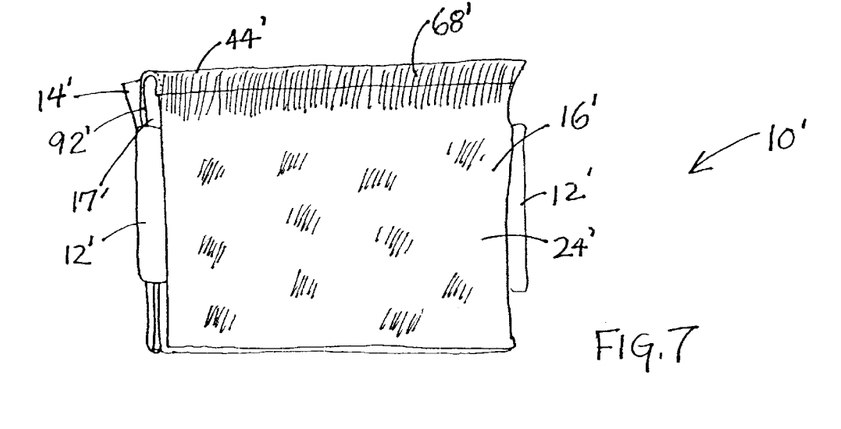
FIG. 7 is a rear perspective view of the tourniquet padding of FIG. 6.
Figure 8:
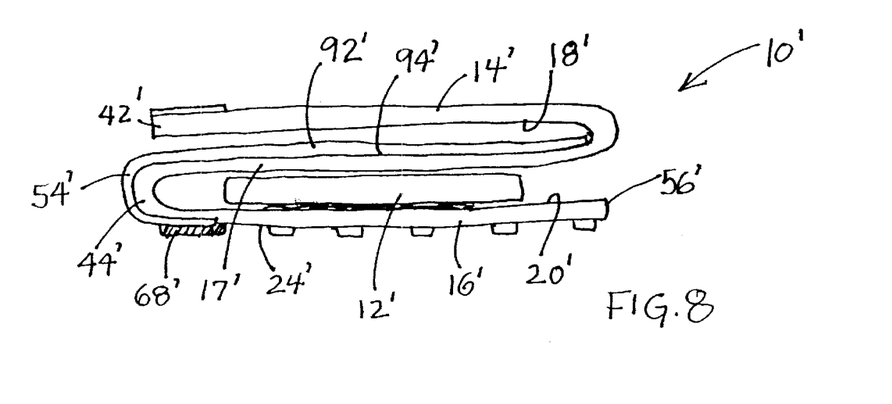
FIG. 8 is a side view of the tourniquet padding of FIG. 6, taken along lines 8—8.

Referring now to FIGS. 6–8, in another embodiment of a tourniquet padding 10' according to the invention, the surfaces directed "down" the extremity (distally) are made to be waterproof, so that the prepping and other solutions used in surgery are not absorbed and/or wicked into the tourniquet padding positioned underneath the tourniquet. As depicted, a layer 92' of a liquid-repellent material has been bonded to the surface 94' of the inner sheet 17' and extends over the distal edge 44' and onto at least a portion of the outer surface 24' of the second (inner) cover sheet 16'. Suitable liquid-repellent materials include those that repel and/or are impermeable or impervious to liquids, including, for example, polyethylene or other plastic sheeting material. As shown in FIG. 8, the adhesive layer 68' along the distal edge 44' on the outer surface 24' of the second cover sheet 16' is then applied onto the plastic sheeting 92'.

Figure 9:
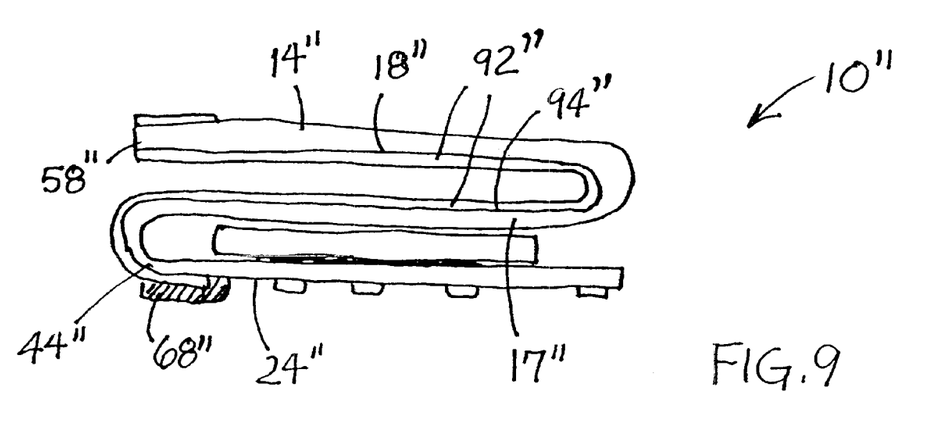
FIG. 9 is a side view of another embodiment of the tourniquet padding of FIG. 6, taken along lines 8—8, showing an extension of the liquid-impermeable layer.

The portion of the first (upper) cover sheet applied to the tourniquet helps protects at least the distal edge of the tourniquet from extraneous liquids and other materials that can soil the tourniquet. To that end, as depicted in FIG. 9, it is preferred that the liquid-repellent layer 92" is applied to the first inner surface 18" of the first cover sheet 14". When the distal portion 58" of the first cover sheet 14" is adhered onto the tourniquet, the plastic sheeting 92" will provide a protective covering for at least the distal edge of the tourniquet. More complete coverage of the surface of the tourniquet can be achieved by widening the first cover sheet 14" and attaching the distal portion 58" at or near the proximal edge of the tourniquet.

Although not shown, a liquid-repellent layer can be bonded only to the cover sheet, for example, the inner surface (18') of the first (upper) cover sheet and/or the inner surface (20') of the second (inner) cover sheet, and not over the distal edges (42', 44') to make only the surfaces of the cover sheets waterproof.

Figure 10:
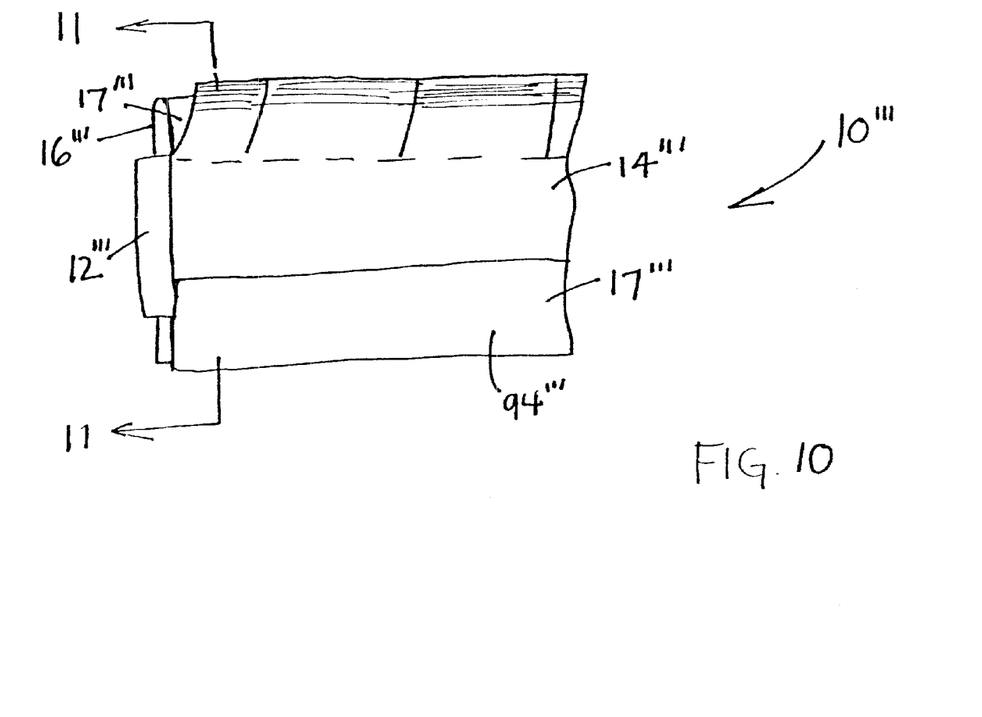
FIG. 10 is a front perspective view of another embodiment of a tourniquet padding of the invention showing the cover sheet attached to an inner sheet layer.
Figure 11:
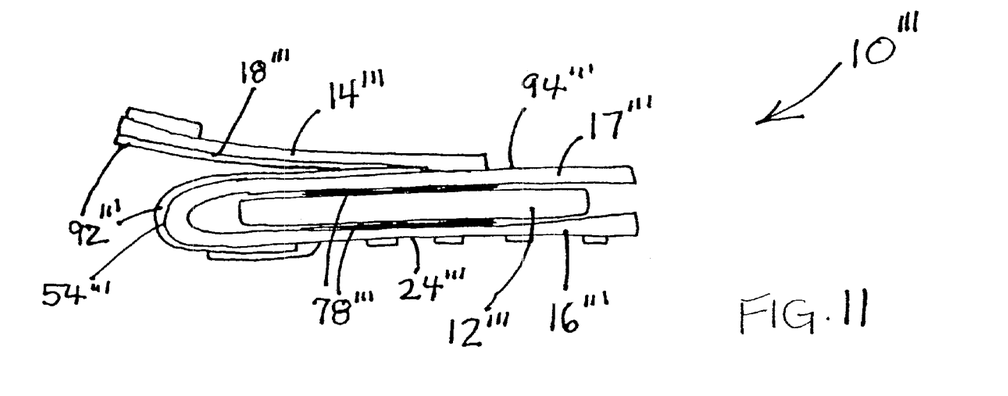
FIG. 11 is a side view of the tourniquet padding of FIG. 6, taken along lines 11—11.

Another embodiment of a tourniquet padding 10''' according to the invention is shown in FIGS. 10–11. The tourniquet padding comprises a unitary sheet that is folded into at least two layers to form the second (inner) cover sheet 16''' and at least one overlying (inner) layer 17'''. A padding material 12''' is disposed between and attached by adhesive areas 78'' to the inner layer 17''' and the second cover sheet 16'''. The first (outer) cover sheet 14''' is attached to the surface 94''' of the inner layer 17'''. As also shown, a liquid-impermeable sheet 92''' is affixed to the inner surface 18''' of the first cover sheet 14''' to protect the surface of the tourniquet during a procedure. A liquid-impermeable sheet 92''' is also shown affixed to the surface 94''' of the inner layer 17''', and extends over the distal edge 54''' of the tourniquet padding and onto the outer surface 24''' of the second cover sheet to protect the padding material 12''' from becoming wet.

Figure 12:
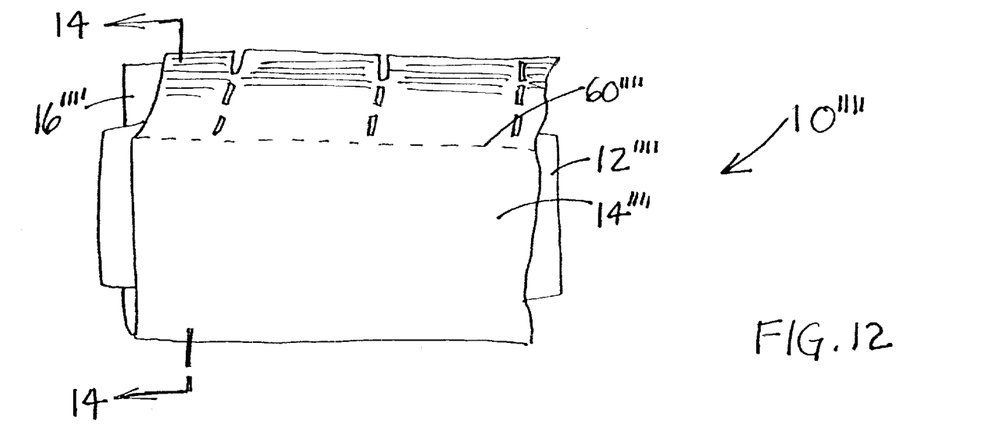
FIG. 12 is a front perspective view of another embodiment of a tourniquet padding of the invention.
Figure 13:
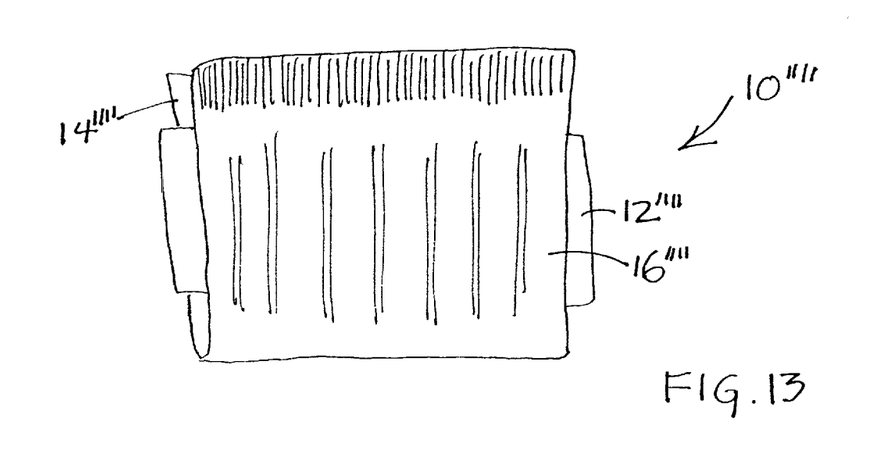
FIG. 13 is a rear perspective view of the tourniquet padding of FIG. 12.
Figure 14:
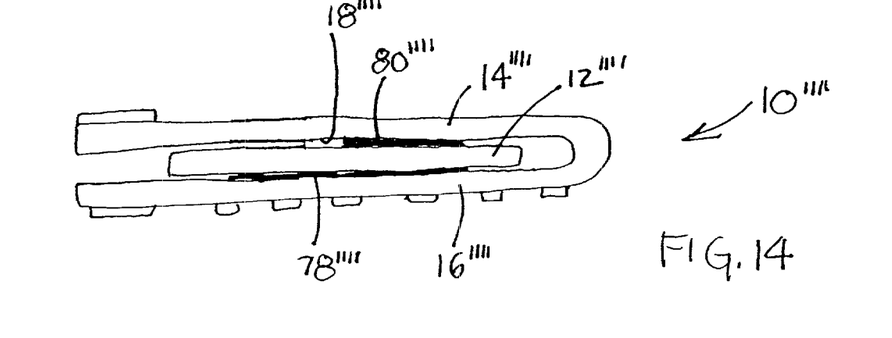
FIG. 14 is a side view of the tourniquet padding of FIG. 12, taken along lines 14—14.
Figures 15A, 15B, 16A, 16B:
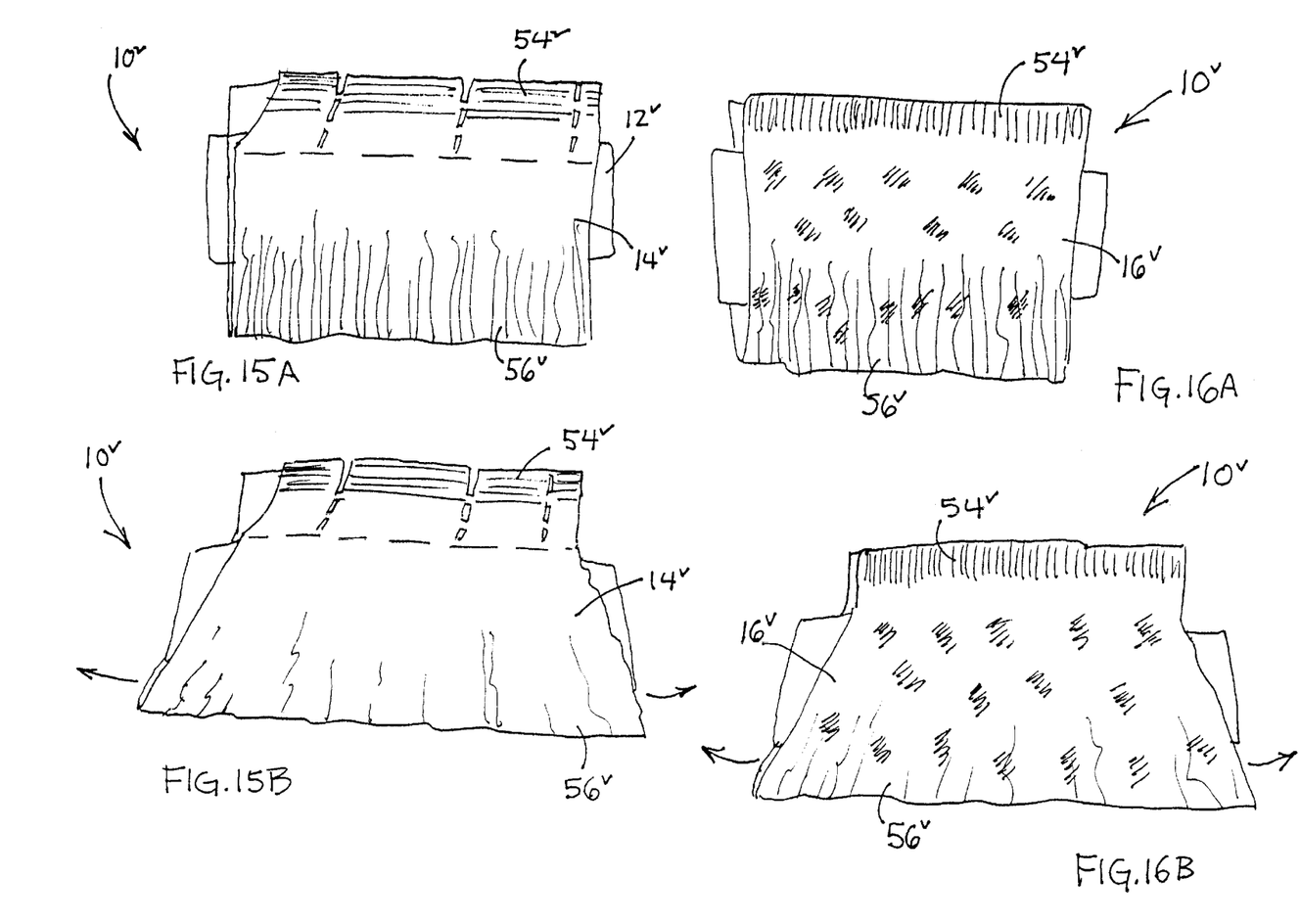
FIGS. 15A–15B are front perspective views of another embodiment of a tourniquet padding of the invention having a gathered proximal edge, with FIG. 15B showing the proximal edge of the padding extended.
FIGS. 16A–16B are rear perspective views of the tourniquet padding of FIGS. 15A–15B, with FIG. 16B showing the proximal edge of the padding extended.

Yet another embodiment of a tourniquet padding 10'''' according to the invention is shown in FIGS. 12–14. As depicted, the cover sheets 14'''', 16'''' are shown as a unitary sheet that is folded in about half with the padding material 12'''' sandwiched therebetween. The padding layer 12'''' is positioned between and affixed to the second (lower) cover layer 16'''', for example by an adhesive bonding 78''''. A portion of the inner surface 18'''' of the first (upper) cover sheet 14'''' (proximal to the fold line 60'''') is also shown as bonded to the padding layer 12'''' by adhesive area 80''''.

The tourniquet padding can also have an element of elasticity to accommodate its application to a range of sizes of extremities having varying circumferences. For example, in another embodiment, the cover sheets of the tourniquet padding may be gathered to make it slightly elastic in order to accommodate extremities (arm/leg) of varying diameter or circumference. As depicted in FIGS. 15A–16A, the cover sheets 14ᵛ, 16ᵛ of the tourniquet padding 10ᵛ are pleated or crimped along the proximal edge 56ᵛ. When the tourniquet padding is then wrapped around a limb of a person, the cover sheets may be spread/extended along the proximal edge, as shown by the arrows in FIGS. 15B–16B, to wrap around a portion of the limb having a wider circumference than at the distal edge 54ᵛ of the tourniquet padding.

Figures 17A, 17B:
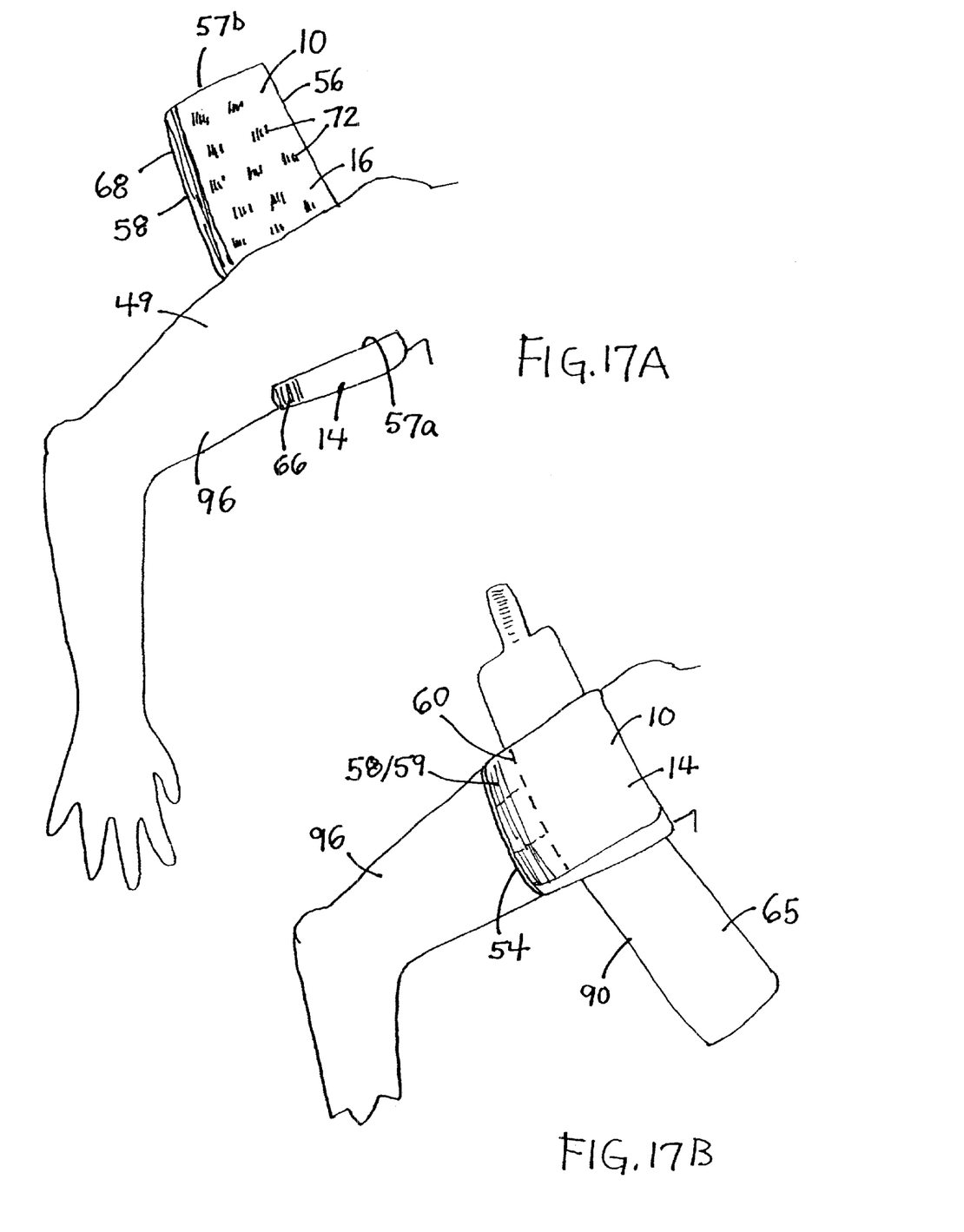
FIGS. 17A–17E are views of the tourniquet padding of FIG. 1 at sequential steps of applying the tourniquet padding and a tourniquet on the upper arm of a person.
Figures 17C, 17D, 17E:
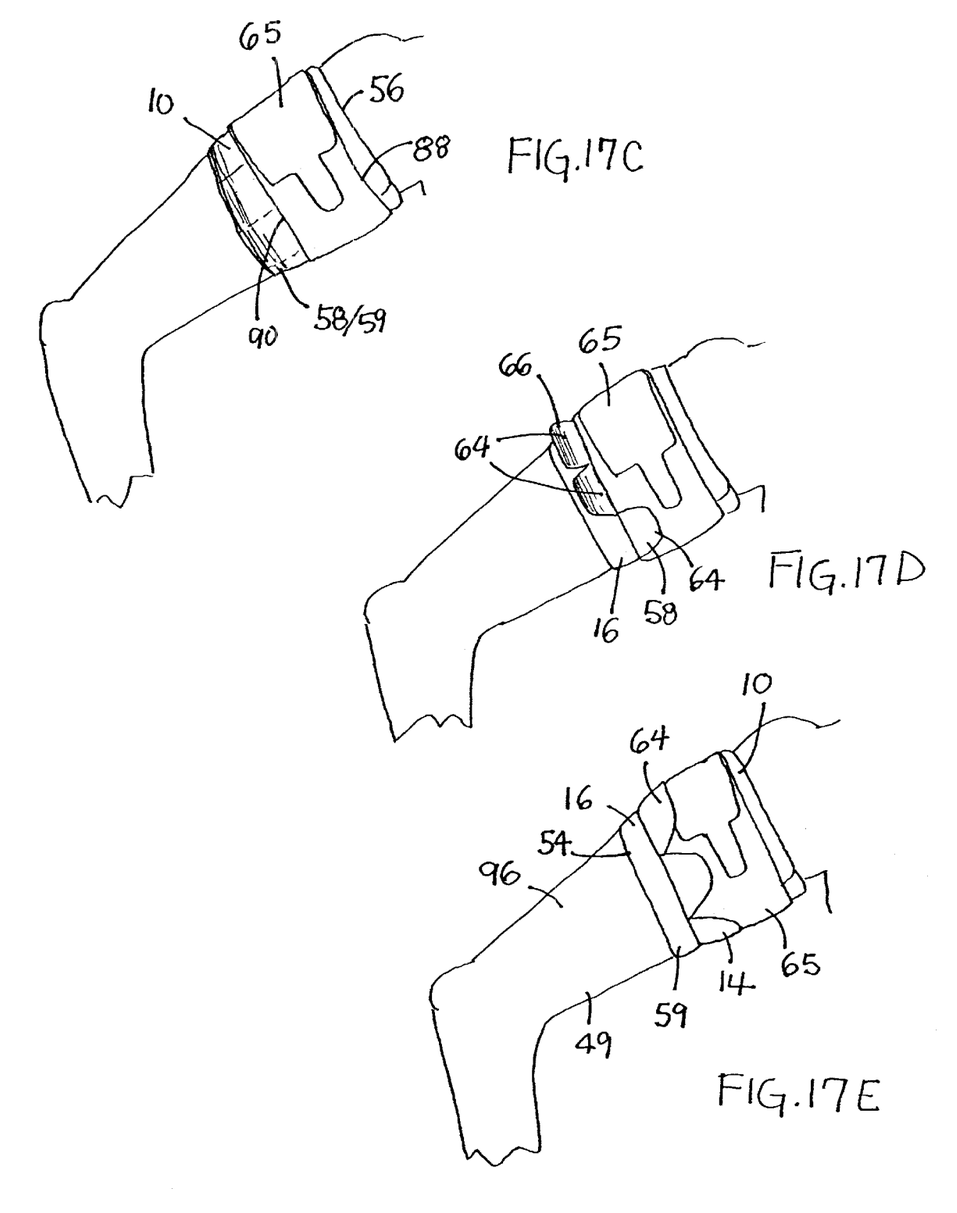

A use of the tourniquet padding 10 depicted in FIGS. 1–5 is shown in FIGS. 17A–17E. The releasable sheet 76a is first removed from the adhesive strip 68 and adhesive areas 72 on the second (inner) cover sheet 14. As shown in FIGS. 17A–17B, the tourniquet padding 10 is then wrapped around the limb 96 of the person, shown as the upper extremity, preferably with the ends 57a, 57b slightly overlapping, and the adhesive areas 68, 72 on the second cover sheet 16 are secured to the skin 49. A tourniquet 65 is then wrapped around the tourniquet padding 10 such that the distal edge 90 of the tourniquet is at or near the fold line 60 of the first cover sheet 14. As shown in FIG. 17C, the distal edge portions 58, 59 of the first and second cover sheets 14, 16 extend beyond the distal edge 90 of the tourniquet. The proximal edge 56 of the tourniquet padding also extends beyond the proximal edge 88 of the tourniquet.

As depicted in FIG. 17D, the distal portion 58 of the first cover sheet 14 is then turned proximally over the lower or distal edge 90 of the tourniquet 65, and adhered to the tourniquet by means of the adhesive 66. This keeps the tourniquet from slipping down the arm/leg, protects it from fluids used for prepping the skin, and generally keeps the tourniquet clean. As depicted, the distal portion 58 has been separated into sections or flaps 64 by means of the perforated lines 62. As shown in FIG. 17E, the tourniquet 65 is thus securely positioned over the tourniquet padding 10 around the limb 96 of the user, and can be inflated and deflated with no or minimal slipping down the limb of the person.

In the use of the tourniquet padding depicted in FIGS. 6–9, the inclusion of a liquid-impermeable layer 92'' in the design of the device helps prevent liquids that may be applied to the limb from coming into contact with the padding. Referring to FIG. 17E, the adherence of the distal portion 59 of the second (inner) cover sheet 16 to the skin and the presence of a liquid-impermeable layer (not shown) over the distal edge 54 of the tourniquet padding substantially prevents liquid from contacting the portion of the padding underlying the tourniquet 65.

The invention has been described by reference to detailed examples and methodologies. These examples are not meant to limit the scope of the invention. It should be understood that variations and modifications may be made while remaining within the spirit and scope of the invention, and the invention is not to be construed as limited to the specific embodiments shown in the drawings.

What is claimed:

1. A tourniquet padding, comprising:
   padding material disposed between a first and second cover sheet; each of the cover sheets having an inner and outer surface, a length and a width, and distal and proximal edges extending along the length;
   the cover sheets each having adhesive disposed on the outer surface along the distal edge; the second cover sheet further comprising one or more adhesive portions disposed on the outer surface;
   the tourniquet padding having a length sufficient to be wrapped around a limb of a person; and the cover sheets having a width wider than a tourniquet such that a portion of the first cover sheet along the distal edge may be folded onto and adhered to an outer surface of the tourniquet when positioned on the tourniquet padding; and the second cover sheet may be adhered to the skin of the person such that the tourniquet padding and tourniquet are maintained substantially in place on the limb of the person during use without slipping.

2. The tourniquet padding of claim 1, comprising comprise a unitary sheet folded into at least three overlying layers to form the first and second cover sheets and one or more inner layers; and the padding is disposed between the second cover layer and an inner layer.

3. The tourniquet padding of claim 1, comprising a unitary sheet folded into at least two layers to form the second cover sheet and one or more overlayers, and the first cover sheet affixed to an uppermost overlayer.

4. The tourniquet padding of claim 1, wherein the padding layer provides a cushioning sufficient to prevent the skin of a person from being pinched by a tourniquet mounted on the tourniquet padding when wrapped around a limb of the person.

5. A tourniquet padding, comprising:
   a unitary sheet folded into at least three layers comprising a first outer cover layer, a second outer cover layer, and one or more inner layers; and padding disposed between the second cover layer and an inner layer;
   each of the at least three sheet layers having an inner and outer surface, a length and a width, opposing side edges, and distal and proximal edges extending along the length;
   the first and second outer cover layers each having adhesive disposed on the outer surface along the distal edge; the second outer cover layer further comprising one or more adhesive portions disposed on the outer surface; and the first outer cover layer comprising perforations to separate the distal edge into sections;

the tourniquet padding having a length sufficient to be wrapped around a limb of a person; and the cover sheets having a width wider than a tourniquet such that a portion of the first cover sheet along the distal edge may be folded onto and adhered to an outer surface of the tourniquet when positioned on the tourniquet padding; and the second cover sheet may be adhered to the skin of the person such that the tourniquet padding and tourniquet are maintained substantially in place on the limb of the person during use without slipping; and the padding layer provides a cushioning sufficient to prevent the skin of a person from being pinched by the tourniquet.

6. The tourniquet padding of claim 5, further comprising a layer of a liquid-impermeable material affixed to the inner surface of the first outer cover sheet, over the distal edge of the second outer cover sheet, or a combination thereof.

7. A tourniquet padding, comprising:
a unitary sheet folded into at least three layers comprising an upper cover layer, a lower cover layer, and one or more inner layers disposed between the upper and lower cover layers; and padding disposed between the second cover layer and an inner layer;

each of the at least three layers having an inner and outer surface, a length and a width, opposing side edges, and distal and proximal edges extending along the length;

the upper and lower cover layers each having adhesive disposed on the outer surface along the distal edge; the lower cover layer further comprising one or more adhesive portions disposed on the outer surface; and the upper cover layer comprising perforations to separate the distal edge into sections;

the tourniquet padding having a length sufficient to be wrapped around a limb of a person; and the cover sheets having a width wider than a tourniquet such that a portion of the upper cover sheet along the distal edge may be folded onto and adhered to the tourniquet when positioned thereon; and the lower cover sheet may be adhered to the skin of the person such that the tourniquet padding and tourniquet are maintained substantially in place on the limb of the person during use without slipping; and the padding layer provides a cushioning sufficient to prevent the skin of a person from being pinched by the tourniquet.

8. A tourniquet padding, comprising:
a unitary sheet folded into at least two layers to form a lower cover sheet and one or more overlayers; an upper cover sheet affixed to an uppermost overlayer; and padding disposed between the upper and lower cover sheets;

each of the cover sheets having an inner and outer surface, a length and a width, and distal and proximal edges extending along the length;

the cover sheets each having adhesive disposed on the outer surface along the distal edge; the lower cover sheet further comprising one or more adhesive portions disposed on the outer surface;

the tourniquet padding having a length sufficient to be wrapped around a limb of a person; and the cover sheets having a width wider than a tourniquet such that a portion of the upper cover sheet along the distal edge may be folded onto and adhered to an outer surface of the tourniquet when positioned on the tourniquet padding; and the lower cover sheet may be adhered to the skin of the person such that the tourniquet padding and tourniquet are maintained substantially in place on the limb of the person during use without slipping.

9. The tourniquet padding of claim 8, further comprising a layer of a liquid-impermeable material affixed to the inner surface of the upper cover sheet, over the distal edge of the lower cover sheet, or a combination thereof.

10. A tourniquet padding, comprising:
a first and second cover sheet, each of the cover sheets having an inner and outer surface, a length and a width, and distal and proximal edges extending along the length;

the cover sheets each having adhesive disposed on the outer surface along the distal edge; the second cover sheet further comprising one or more adhesive portions disposed on the outer surface;

the tourniquet padding having a length sufficient to be wrapped around a limb of a person; and the cover sheets having a width wider than a tourniquet such that a portion of the first cover sheet along the distal edge may be folded onto and adhered to an outer surface of the tourniquet when positioned on the tourniquet padding; and the second cover sheet may be adhered to the skin of the person such that the tourniquet padding and tourniquet are maintained substantially in place on the limb of the person during use without slipping.

11. The tourniquet padding of claim 10, further comprising padding material disposed between the first and second cover sheets.

12. The tourniquet padding of claim 10, further comprising a layer of a liquid-impermeable material affixed to the inner surface of the first cover sheet, over the distal edge of the second cover sheet, or a combination thereof.

13. The tourniquet padding of claim 10, wherein the first cover sheet comprises perforations, slits, or a combination thereof, to separate the distal edge into sections.

14. A method of applying a tourniquet to a limb of a person, comprising the steps of:
wrapping a tourniquet padding according to claim 10 around a limb of a person such that the adhesive layer and adhesive portions disposed on the outer surface of the second cover sheet of the tourniquet padding are adhered to the limb;

positioning a tourniquet over the tourniquet padding and around the limb of the person, such that the distal edges of the cover sheets extend beyond a distal edge of the tourniquet;

folding a portion of the first cover sheet along the distal edge; and adhering the folded portion of the first cover sheet to the tourniquet.

15. The method of claim 14, wherein the tourniquet padding further comprises padding material disposed between the first and second cover sheets.

16. The method of claim 15, wherein the padding provides a cushioning sufficient to prevent the skin of a person from being pinched by the tourniquet when inflated and deflated.

17. The method of claim 14, wherein the first cover sheet of the tourniquet padding further comprises perforations to separate the distal edge into sections; and the method further comprises, prior to the step of folding the first cover sheet, the step of separating the distal edge of the first cover sheet along the perforations into sections, and folding and adhering the sections of the first cover sheet to the tourniquet.

18. The method of claim 17, further comprising, after the step of adhering the first cover sheet to the tourniquet, the step of inflating and deflating the tourniquet about the limb of the person.

19. The method of claim 18, wherein the adhesive on the outer surface of the second cover sheet is sufficient to maintain the tourniquet padding and tourniquet substantially in place on the limb of the person during use without slipping during the step of inflating and deflating the tourniquet.

20. The method of claim 14, wherein the first cover sheet of the tourniquet padding further comprises a layer of a liquid-impermeable material covering the distal edge of the second cover sheet and affixed to the inner surface and a portion of the outer surface of the second cover sheet, and the liquid impermeable layer substantially prevents a liquid applied to the limb from contacting the padding underlying the tourniquet.

21. The method of claim 14, wherein the liquid-impermeable layer is affixed to the inner surface of the first cover sheet.

22. A cover sheet for a tourniquet padding, comprising:

an elongate sheet of compliant material;

the sheet having an inner and outer surface, a length and a width, opposing side edges, and distal and proximal edges extending along the length;

the sheet comprising adhesive on the outer surface along the distal edge, and perforations to separate the distal edge into sections.

23. The sheet of claim 22, sized for receiving a tourniquet thereon wherein the width of the sheet is wider than the tourniquet such that a portion of the sheet along the distal edge may be folded onto and adhered to the tourniquet when positioned on the sheet, and the proximal edge of the sheet extends beyond the proximal edge of the tourniquet.

24. The sheet of claim 22, wherein the compliant material comprises paper, a scrim reinforced material, cloth, terry cloth, cheesecloth, and combinations thereof.

25. The sheet of claim 22, wherein the compliant material comprises a scrim reinforced material.

26. The sheet of claim 25, wherein the scrim reinforced material comprises fibers at least partially embedded in the material.

27. The sheet of claim 26, wherein the fibers comprise a material selected from the group consisting of fiberglass, ceramic, polyester, polyolefin, polyacrylate, rayon, cotton, hemp, jute, natural rubber, polyurethane, and blends thereof.

28. The sheet of claim 26, wherein the fibers are interwoven at about right angles in an open mesh web.

29. The sheet of claim 22, wherein the sheet is gathered along the proximal edge.

30. A cover sheet for a tourniquet padding, comprising:

an elongate sheet of a compliant material comprising a scrim reinforced material and folded into at least three layers comprising a first outer cover layer, a second outer cover layer, and one or more inner layers; each of the at least three sheet layers having an inner and outer surface, a length and a width, opposing side edges, and distal and proximal edges extending along the length;

the first and second outer cover layers each having adhesive disposed on the outer surface along the distal edge; the second outer cover layer further comprising one or more adhesive portions disposed on the outer surface; and the distal edge of the first outer cover layer being separable into sections.

31. The sheet of claim 30, wherein the scrim reinforced material comprises paper, fiberglass knit, cloth, terry cloth, cheesecloth, and combinations thereof.

32. The sheet of claim 30, wherein the scrim reinforced material comprises filaments at least partially embedded in the material.

33. The sheet of claim 30, wherein the scrim filaments comprise a material selected from the group consisting of fiberglass, ceramic, polyester, polyolefin, polyacrylate, rayon, cotton, hemp, jute, natural rubber, polyurethane, and blends thereof.

34. The sheet of claim 30, sized for receiving a tourniquet thereon wherein the sheet has a width wider than the tourniquet such that a portion of the first outer cover layer along the distal edge may be folded onto and adhered to the tourniquet when positioned on the first outer cover layer, and the sheet has a proximal edge that extends beyond a proximal edge of the tourniquet.

35. The sheet of claim 30, further comprising a liquid-impermeable layer affixed to the inner surface of the first cover sheet, over the distal edge of the second cover sheet and extending onto an overlying inner layer, or a combination thereof.

36. The sheet of claim 30, wherein the distal edge of the first cover layer comprises perforations, slits, or a combination thereof.

* * * * *